US010278614B2

(12) United States Patent
Curran et al.

(10) Patent No.: US 10,278,614 B2
(45) Date of Patent: *May 7, 2019

(54) SYSTEM AND METHOD FOR DETECTING SHEATHING AND UNSHEATHING OF LOCALIZATION ELEMENTS

(71) Applicant: St. Jude Medical, Atrial Fibrillation Division, Inc., St. Paul, MN (US)

(72) Inventors: Timothy G. Curran, Ramsey, MN (US); Anthony D. Hill, Minneapolis, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 274 days.

This patent is subject to a terminal disclaimer.

(21) Appl. No.: 15/208,436

(22) Filed: Jul. 12, 2016

(65) Prior Publication Data

US 2016/0317065 A1 Nov. 3, 2016

Related U.S. Application Data

(63) Continuation of application No. 14/692,305, filed on Apr. 21, 2015, now Pat. No. 9,392,973, which is a
(Continued)

(51) Int. Cl.
| | | |
|---|---|---|
| *A61B 5/042* | (2006.01) | |
| *A61B 5/06* | (2006.01) | |
| *A61B 5/00* | (2006.01) | |

(52) U.S. Cl.
CPC .............. *A61B 5/063* (2013.01); *A61B 5/042* (2013.01); *A61B 5/0422* (2013.01);
(Continued)

(58) Field of Classification Search
CPC ................................ A61B 5/042; A61B 5/063
(Continued)

(56) References Cited

U.S. PATENT DOCUMENTS 5,697,377 A 12/1997 Wittkampf
5,983,126 A 11/1999 Wittkampf
(Continued)

OTHER PUBLICATIONS

International Search Report and Written Opinion for PCT Application No. PCT/US2014/019891, dated May 23, 2014. 12 pgs.
(Continued)

*Primary Examiner* — Carl H Layno
*Assistant Examiner* — Jon Eric C Morales
(74) *Attorney, Agent, or Firm* — Wiley Rein LLP

(57) ABSTRACT

A method of detecting whether a localization element is within or outside of an introducer sheath generally includes obtaining a localization signal from the localization element and detecting the state of the localization element relative to the sheath based upon the quadrature component of the localization signal. A baseline quadrature component is typically established with the localization element outside of the sheath. When the quadrature component deviates from this baseline value, it is indicative of the localization element being within the sheath. Conversely, when the quadrature component remains relatively close to the baseline value, it is indicative of the localization element being outside of the sheath. In an electrophysiology study, the state information can be used to take corrective action with respect to the data being collected.

17 Claims, 5 Drawing Sheets

Related U.S. Application Data continuation of application No. 13/785,807, filed on Mar. 5, 2013, now Pat. No. 9,026,196.

(52) U.S. Cl.
CPC .......... *A61B 5/6852* (2013.01); *A61B 5/6885* (2013.01); *A61B 5/746* (2013.01)

(58) Field of Classification Search
USPC ........................................ 600/424, 374, 448
See application file for complete search history.

(56) References Cited

U.S. PATENT DOCUMENTS

| | | |
|---|---|---|
| 6,640,119 B1 | 10/2003 | Budd |
| 6,728,562 B1 | 4/2004 | Budd |
| 6,939,309 B1 | 9/2005 | Beatty |
| 6,947,785 B1 | 9/2005 | Beatty |
| 6,978,168 B2 | 12/2005 | Beatty |
| 6,990,370 B1 | 1/2006 | Beatty |
| 7,263,397 B2 | 8/2007 | Hauck |
| 7,885,707 B2 | 2/2011 | Hauck |
| 9,026,196 B2 * | 5/2015 | Curran .................. A61B 5/063 600/374 |
| 2004/0254437 A1 | 12/2004 | Hauck |
| 2007/0213616 A1 * | 9/2007 | Anderson .............. A61B 50/13 600/448 |
| 2008/0255470 A1 | 10/2008 | Hauck et al. |
| 2009/0262109 A1 | 10/2009 | Markowitz et al. |
| 2013/0303886 A1 | 11/2013 | Ludwin et al. |
| 2014/0257071 A1 | 9/2014 | Curran et al. |

OTHER PUBLICATIONS

International Search Report for PCT Application No. PCT/US2016/031106, dated Jul. 21, 2016. 5 pgs.

* cited by examiner

SYSTEM AND METHOD FOR DETECTING SHEATHING AND UNSHEATHING OF LOCALIZATION ELEMENTS

CROSS-REFERENCE TO RELATED APPLICATIONS

This application is a continuation of U.S. application Ser. No. 14/692,305, is now U.S. Pat. No. 9,392,973, filed 21 Apr. 2015, which is a continuation of U.S. application Ser. No. 13/785,807, filed 5 Mar. 2013, which is hereby incorporated by reference as though fully set forth herein.

BACKGROUND a. Field of the Invention

The instant disclosure relates to localization systems, such as those used in cardiac diagnostic and therapeutic procedures. In particular, the instant disclosure relates to systems, apparatuses and methods for detecting when a localization element(s), such as an electrode(s), emerges from and/or is retracted into an introducer sheath or other enveloping instrument.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. In many instances, the catheters are inserted into the body and navigated to the target location with the aid of an introducer sheath (sometimes referred to as simply an "introducer" or a "sheath"). As the ordinarily skilled artisan will appreciate, an introducer is a catheter with a central lumen through which other medical devices can be passed.

It is also known to track the three-dimensional coordinates of a catheter or other medical device moving within a patient's body using a localization system (sometimes also referred to as a "mapping system," "navigation system," or "positional feedback system"). These devices typically use magnetic, electrical, ultrasound, and other radiation sources to determine the coordinates of these devices. For example, impedance-based localization systems determine the coordinates of the medical device by interpreting a voltage measured by the medical device (more particularly, the voltages measured by one or more electrodes carried on the medical device) as a location within an electrical field.

One drawback of an impedance-based system, however, is that the impedance measurements become unreliable when the medical device is withdrawn into the introducer. This is because the introducer is normally made of an insulating material, such that the voltage gradient in the vicinity of localization electrodes within the sheath becomes non-linear and erratic. Indeed, a localization electrode within a sheath may appear to wander widely, making it difficult for the localization system to accurately and precisely render an image of the medical device for the practitioner. Although visual recognition of this condition is possible, there is no extant system or method to do so analytically.

BRIEF SUMMARY

Among other things, the disclosure provides an analytical method(s) to detect a localization element/sheath state change (e.g., the emergence of a localization electrode from or withdrawal of a localization electrode into an introducer).

The disclosure also provides an analytical method(s) to identify the position of a localization element(s) relative to an introducer (e.g., whether the localization element(s) is/are within, or outside of, the introducer).

Further, a localization system is disclosed that analytically detects localization element/sheath state changes.

Also disclosed herein is a localization system that analytically determines the relative position of a localization element(s) to an introducer sheath.

In one aspect, a method of detecting a localization element/sheath state change with a localization system includes the following steps: establishing a localization field using a plurality of localization field generators; obtaining at least one localization signal from at least one catheter-borne localization element positioned within the localization field via an introducer sheath, the at least one localization signal including an in-phase component and a quadrature component; and detecting a localization element/sheath state change for the at least one catheter-borne localization system based on the quadrature component of the at least one localization signal. The method optionally further includes establishing a baseline quadrature component with the at least one localization element outside of the introducer sheath. In some embodiments, the baseline quadrature component is established by adjusting a demodulation delay for the localization signal until the quadrature component remains substantially constant at a calibration value as the at least one localization element moves. Movement of the localization element can be imparted by patient (e.g., cardiac) motion and/or by catheter motion.

In certain aspects, withdrawal of the at least one localization element into the introducer sheath is detected based upon the quadrature component of the at least one localization signal deviating from the calibrated value by more than a preset amount. Similarly, re-emergence of the at least one localization element from the introducer sheath can be detected based upon the quadrature component of the at least one localization signal returning to within the preset amount of the calibrated value.

Upon detecting withdrawal of the at least one localization element into the introducer sheath, an alert can be generated.

In another aspect, the baseline quadrature component can be established by making a plurality of complex impedance measurements and determining least squares parameters in a linear model. Withdrawal of the at least one localization element into the introducer sheath can then be detected based upon the quadrature component of the at least one localization signal deviating from the linear model by more than a preset amount.

It is also contemplated that the localization signal is measured along an axis defined by a first localization field generator and a second localization field generator, relative to a reference point substantially aligned with the axis, where the at least one catheter-borne localization element is spaced apart from the reference point along the axis. For example, the first localization generator can be positioned on a patient's neck, the second localization field generator can be positioned on the patient's leg, the reference point can be on the patient's belly, and the at least one catheter-borne localization element can be positioned within the patient's heart.

In a further aspect, a method of conducting a cardiac electrophysiology study includes: establishing an impedance-based localization field encompassing a patient's body; obtaining a localization signal from at least one localization element on at least one medical device positioned in the patient's body via an introducer sheath, the localization signal including an in-phase component reflecting a position of the at least one localization element within the localization field and a quadrature component; and detecting whether the at least one localization element is within or outside of the introducer sheath based upon the quadrature component of the localization signal.

The method can also include suspending data collection from the at least one localization element if the at least one localization element is detected within the introducer sheath. Alternatively, the method can include discarding data collected by the at least one localization element when the at least one localization element is detected within the introducer sheath. As still another option, the method can include generating an alert if the at least one localization element is detected within the introducer sheath.

The method typically includes establishing a baseline quadrature component with the at least one localization element positioned outside of the introducer sheath. This can be accomplished, for example, by adjusting a demodulation delay for the localization signal until the quadrature component remains substantially constant at a calibration value as the at least one localization element moves. Then, whether the at least one localization element is within or outside of the introducer sheath can be determined by detecting that the at least one localization element is outside of the introducer sheath when the quadrature component falls within a preset range about the calibration value and detecting that the at least one localization element is within the introducer sheath when the quadrature component falls outside of a preset range about the calibration value.

Also disclosed herein is a localization system including: a localization processor configured to receive as input a localization signal from at least one localization element and to resolve the localization signal into an in-phase component reflective of a position of the at least one localization element and a quadrature component; and a localization element/sheath state change detection processor configured to receive as input the quadrature component and detect a localization element/sheath state change therefrom.

An exemplary advantage of the present invention is that it provides an analytical method of detecting a localization element/sheath state change, reducing the burden on the practitioner to visually recognize such conditions.

Another representative advantage of the present invention is that it provides a localization system with an analytical capability to suspend an electrophysiology study when a localization element is withdrawn into the introducer, thereby rendering its measurements less reliable.

Still another representative advantage of the present invention is that it provides a localization system with an analytical capability to discard electrophysiology study data collected by a localization element within the introducer, thereby rendering its measurements less reliable.

The foregoing and other aspects, features, details, utilities, and advantages of the present invention will be apparent from reading the following description and claims, and from reviewing the accompanying drawings.

DETAILED DESCRIPTION

The present invention provides methods, apparatuses and systems for detecting when a localization element, such as a localization electrode, emerges from and/or is withdrawn into another device such as an introducer sheath (referred to herein as a "localization element/sheath state change"). For purposes of illustration, embodiments of the invention will be described in detail herein in the context of a localization system utilized in a cardiac electrophysiology procedure. It is contemplated, however, that the present invention may be practiced to good advantage in other contexts.

Figure 1:
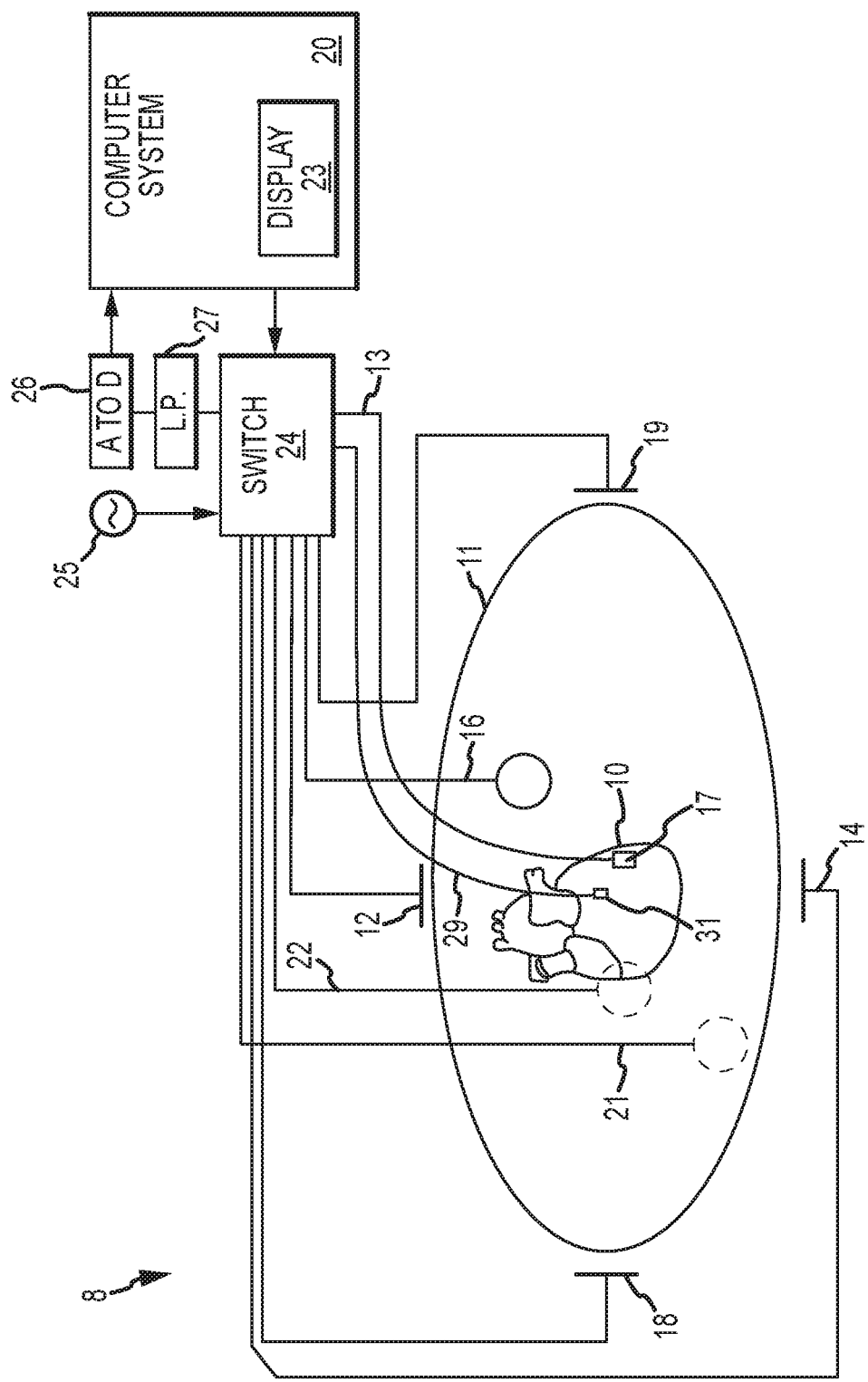
FIG. 1 is a schematic diagram of a localization system, such as may be used in an electrophysiology study.

FIG. 1 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, localization system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG") system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, localization system 8 may comprise sixty-four electrodes on twelve catheters disposed within the heart and/or vasculature of the patient. Of course, this embodiment is merely exemplary, and any number of electrodes and catheters may be used within the scope of the present invention. Likewise, it should be understood that catheter 13 (or multiple such catheters) are typically introduced into the heart and/or vasculature of the patient via one or more introducers (not shown in FIG. 1, but readily understood by the ordinarily skilled artisan)

Figure 2:
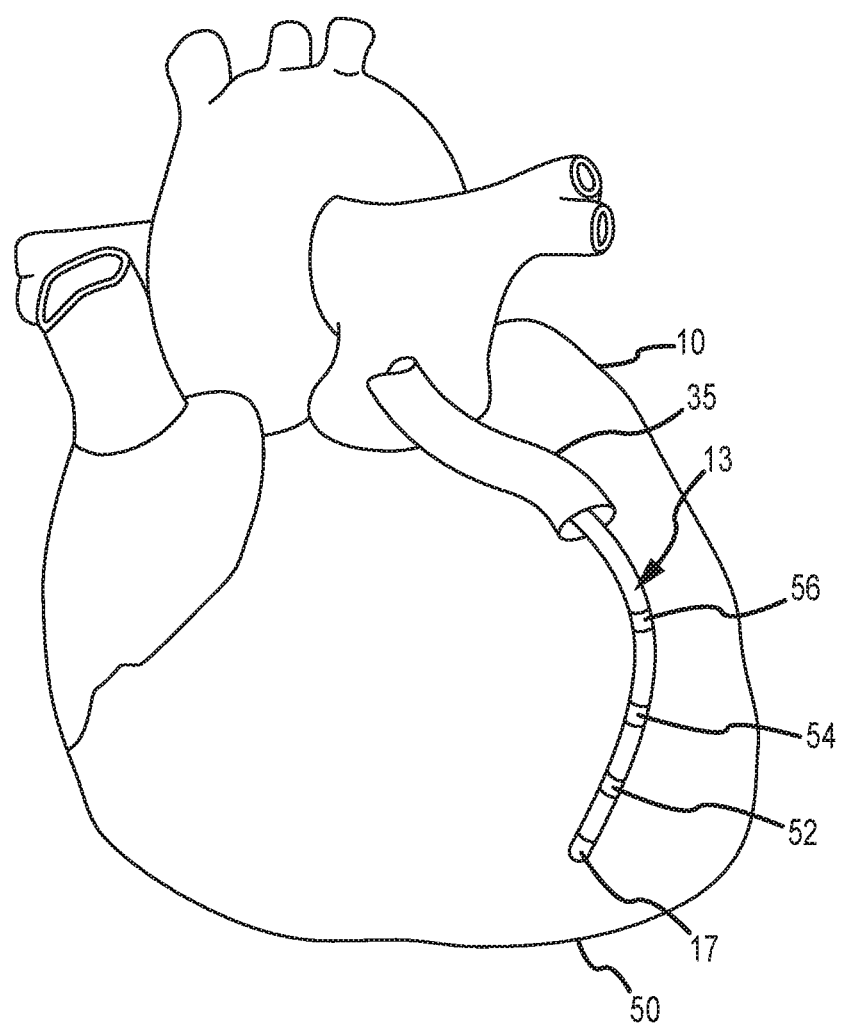
FIG. 2 depicts an exemplary catheter used in an electrophysiology study.

For purposes of this disclosure, a segment of an exemplary catheter 13 is shown in FIG. 2. In FIG. 2, catheter 13 extends into the left ventricle 50 of the patient's heart 10 through an introducer 35, the distal-most segment of which is shown in FIG. 2. The construction of introducers, such as introducer 35, are well known and will be familiar to those of ordinary skill in the art, and need not be further described herein.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by localization system 8.

Figure 3A:
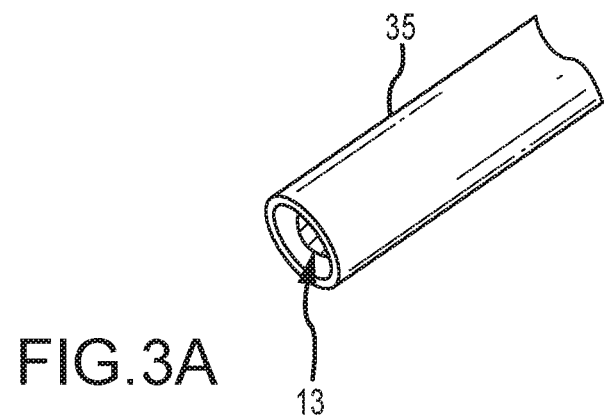
FIGS. 3A through 3C are exemplary perspective views of relative positions of localization electrodes and an introducer sheath.
Figure 3B:
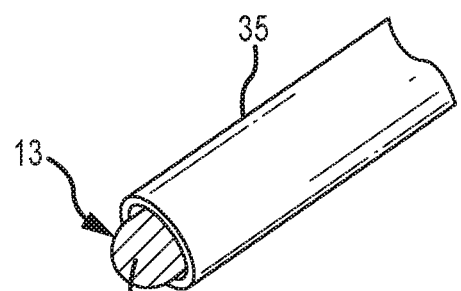
Figure 3C:
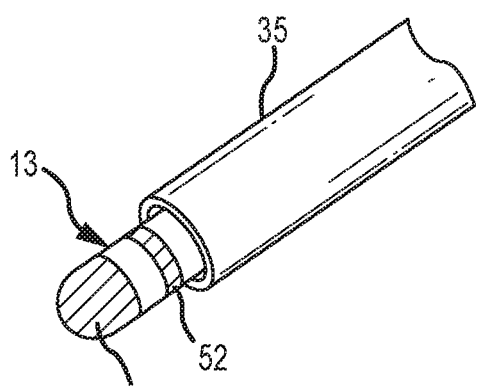

FIGS. 3A through 3C illustrate three relative positions of the distal end of catheter 13 relative to introducer 35. As shown in FIG. 3A, catheter 13 is fully withdrawn into sheath 35 (e.g., electrodes 17, 52, 54, and 56 are all within sheath 35). In FIG. 3B, catheter 13 has been advanced such that electrode 17, but not electrodes 52, 54, and 56, have emerged from sheath 35. In FIG. 3C, catheter 13 has been advanced further, such that electrodes 17 and 52, but not electrodes 54 and 56, have emerged from sheath 35. As discussed in further detail below, the teachings herein can be applied to good advantage to detect the localization element/sheath state changes of electrode 17 from FIG. 3A to FIG. 3B, and of electrode 52 from FIG. 3B to FIG. 3C (and, as the ordinarily skilled artisan will appreciate, vice versa).

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to the multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization, system 8 measures positions. Data sets from each of the surface electrodes, the internal electrodes, and the virtual electrodes may all be used to deter mine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52,

54, 56 relative to the origin. Preferably, the coordinate system is a three-dimensional (x, y, z) Cartesian coordinate system, though the use of other coordinate systems, such as polar, spherical, and cylindrical coordinate systems, is within the scope of the invention.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Patent Application Publication No. 2004/0254437 (now U.S. Pat. No. 7,263,397), which are hereby incorporated herein by reference in their entireties. The electrode data may also be used to compensate for changes in the impedance of the body of the patient as described in U.S. Pat. No. 7,885,707, which is also incorporated herein by reference in its entirety.

Therefore, in one representative embodiment, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In some embodiments, the localization/mapping system is the EnSite™ Velocity™ cardiac mapping system of St. Jude Medical, Inc., which generates electrical fields as described above, or another localization system that relies upon electrical fields. Other localization systems, however, may be used in conjunction with such electrical-field based localization systems in connection with the present teachings, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Thus, the present invention will be described in the context of a localization system that generates an electrical field. The fields generated by localization system 8 will be referred to generically as "localization fields," while the elements generating the fields, such as surface electrodes 12, 14, 16, 18, 19, and 22 will be generically referred to as "localization field generators." As described above, surface electrodes 12, 14, 16, 18, 19, and 22 may also function as detectors to measure the characteristics of the localization field (e.g., the voltages measured at roving electrodes 17, 52, 54, 56, or a current from roving electrodes 17, 52, 54, 56), and thus may also be referred to generically as "localization elements" (or, in the case of an impedance-based localization system, more specifically as "localization electrodes"). Further, the measurements of each localization element can be referred to generically as "localization signals."

As previously described, surface electrodes 12, 14, 16, 18, 19, 22 generate electric fields that are in turn sensed by electrodes 17, 52, 54, and 56 on catheter 13. Signal generator 25 provides an excitation signal to any pair of surface electrodes in the form of a sinusoidal alternating current at, for example, a frequency of 8 kHz, although the ordinarily skilled artisan will appreciate that a broad range of frequencies can be used without departing from the teachings herein.

To determine the electric field intensity at each catheter electrode, the sensed signals are first frequency limited by low-pass filter 27, then converted to a digital value by analog to digital converter 26. Synchronous demodulation is then applied to determine the resulting electric field intensity for each electrode and, in turn, each surface electrode pair. Synchronous demodulation is an established method of determining the intensity of a signal at a particular frequency by multiplying the sensed signal (from analog-to-digital converter 26) with an in-phase copy of the excitation signal from signal generator 25. This in-phase copy is known as the sine reference. Before multiplication, the sine reference is time delayed to phase align it with the sensed signal. The sensed signal has a natural time delay relative to the sine reference due to the electrical path the sensed signal must traverse from signal generator 25, through surface electrodes, body tissue, catheter electrodes, and sensing electronics. The product of the multiplication is averaged of a time period to provide a value that is proportional to the electric field at each catheter electrode. This is the in-phase component and is used to calculate the relative location of each catheter electrode.

By multiplying the same sensed signal with a signal that is 90 degrees out-of-phase with the sine reference (by definition, a cosine reference) signal, an out-of-phase component is determined. This out-of-phase component is also known as the quadrature component.

In a properly tuned localization system (i.e., a system where the demodulation delay time is optimized), the in-phase component will dominate over the quadrature component. The quadrature component, however, will still be measurable. Moreover, provided the localization elements remain outside the introducer sheath, the quadrature component will be substantially constant, regardless of localization element location.

When a localization element is withdrawn into the introducer sheath, however, the quadrature component changes measurably. This is due to the impedance change in the vicinity of the localization element. The impedance change results not only from the constricted space and insulating material construction of the introducer sheath, but also from changes in complex impedance (e.g., a combination of resistance and capacitance).

As the ordinarily skilled artisan will appreciate, changes in capacitance change the delay time of a signal sensed by a localization element. It follows that the demodulation delay time is no longer optimized, leading to position sensitivity in the quadrature component. The same lack of optimization renders the in-phase signal unreliable, leading, for example, to difficulties in rendering an image of catheter 13 within the patient's heart. In one embodiment, when a localization element has been withdrawn into the sheath, it may be desirable to detect this transition to enable the transitioning localization element to be temporarily turned off or otherwise disabled as described further below.

Figure 4:
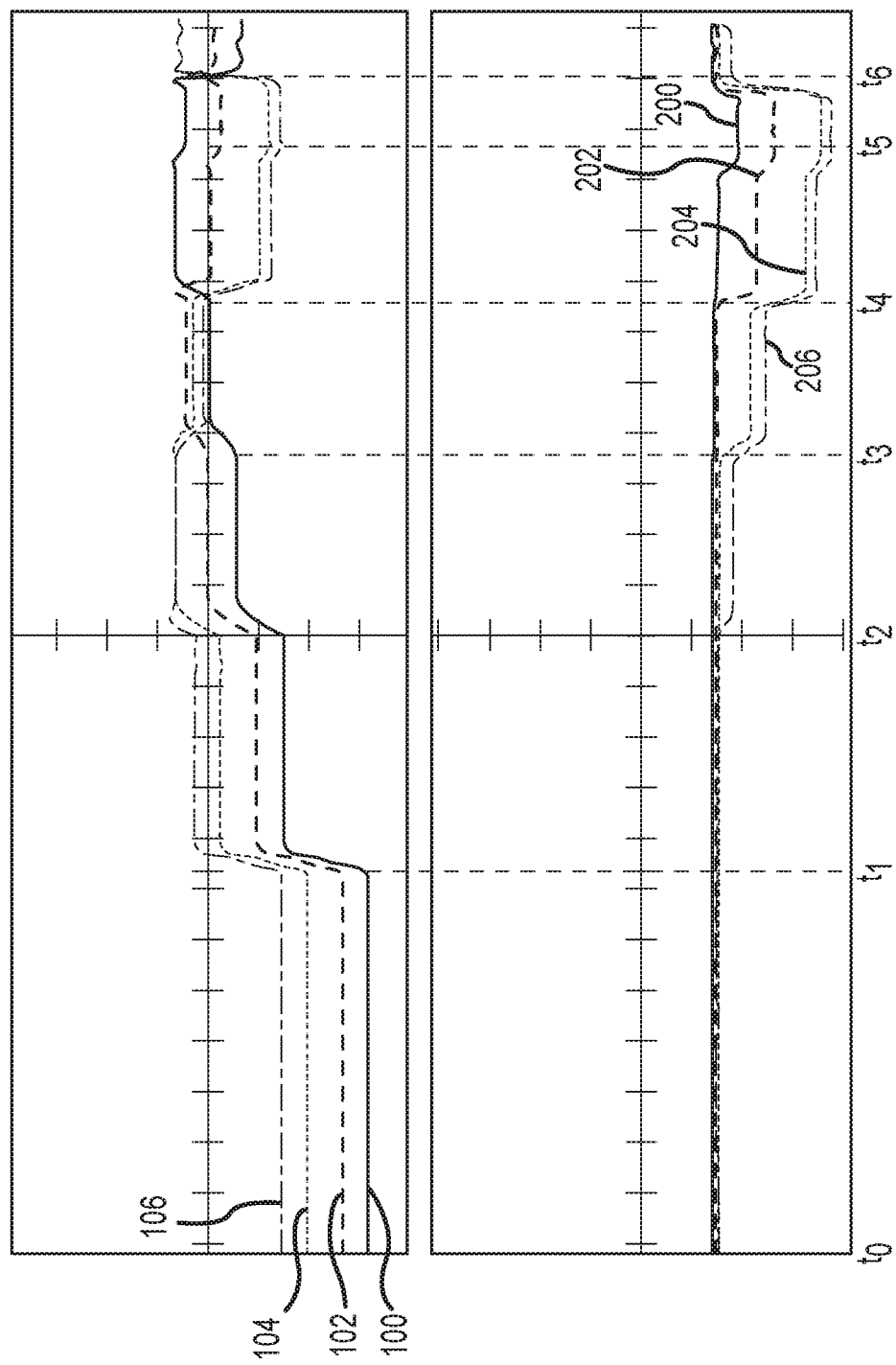
FIG. 4 depicts the in-phase and quadrature components of the localization signals for four localization electrodes.

A method for detecting a localization element/sheath state change based on the quadrature component will now be described with reference to FIGS. 4 and 5. FIG. 4 depicts both the in-phase and quadrature components of the localization signals for four electrodes (e.g., 17, 52, 54, and 56) along the neck-leg axis defined by patch electrodes 18 and 19. The top window of FIG. 4 illustrates the respective in-phase components (100, 102, 104, 106) for these electrodes, while the bottom window illustrates their respective quadrature components (200, 202, 204, 206). At the leftmost edge of FIG. 4 (e.g., time $t_0$), all four electrodes 17, 52, 54, 56 are outside of introducer sheath 35. As can be seen in the lower window of FIG. 4, the quadrature component for each of electrodes 17, 52, 54, 56 is non-zero, relatively small, and substantially constant.

At time $t_1$, approximately 4 seconds later, catheter 13 is partially withdrawn into introducer sheath 35. The top window of FIG. 4 shows the displacement change for each electrode, but, because all four electrodes remain outside of introducer sheath 35, the lower window of FIG. 4 shows no change in the quadrature component for any of the electrodes.

At time $t_2$, approximately 2 seconds later, catheter 13 is withdrawn further into introducer sheath 35 to such an extent that electrode 56 re-enters introducer sheath 35. The top window of FIG. 4 shows the displacement, and further shows an unreliable in-phase component for electrode 56 (line 106). The bottom window of FIG. 4 also shows a measurable change in the quadrature component for electrode 56 (line 206). This measurable change in the quadrature component for electrode 56 is indicative of the localization element/sheath state change for electrode 56.

At time $t_3$, approximately 2 seconds later, catheter 13 is withdrawn further into introducer sheath 35 to such an extent that electrode 54 also re-enters introducer sheath 35. The top window of FIG. 4 shows the displacement, and further shows an unreliable in-phase component for electrode 54 (line 104). The bottom window of FIG. 4 also shows a measurable change in the quadrature component for electrode 54 (line 204), as well as a further change in the quadrature component for electrode 56. This measurable change in the quadrature component for electrode 54 is indicative of the localization element/sheath state change for electrode 54.

At time $t_4$, approximately 1.5 seconds later, catheter 13 is withdrawn further into introducer sheath 35 to such an extent that electrode 52 also re-enters introducer sheath 35. The top window of FIG. 4 shows the displacement, and further shows an unreliable in-phase component for electrode 52 (line 102). The bottom window of FIG. 4 also shows a measurable change in the quadrature component for electrode 52 (line 202), as well as further changes in the quadrature components for electrodes 56, 54. This measurable change in the quadrature component for electrode 52 is indicative of the localization element/sheath state change for electrode 52.

At time $t_5$, approximately 1 second later, catheter 13 is withdrawn further into introducer sheath 35 to such an extent that electrode 17 also re-enters introducer sheath 35. The top window of FIG. 4 shows the displacement, and further shows an unreliable in-phase component for electrode 17 (line 100). The bottom window of FIG. 4 also shows a measurable change in the quadrature component for electrode 17 (line 200), as well as further changes in the quadrature components for electrodes 56, 54, 52. This measurable change in the quadrature component for electrode 17 is indicative of the localization element/sheath state change for electrode 17.

Finally, at time $t_6$, approximately 1 second later, catheter 13 is advanced back out of introducer sheath 35 such that only the most proximal electrode 56 remains within introducer sheath 35. The top window of FIG. 4 shows the displacement, with the in-phase components for electrodes 17, 52, and 54 (lines 100, 102, 104, respectively) returning to reliable signals. Likewise, the bottom window of FIG. 4 shows that the quadrature components for electrodes 17, 52, and 54 (lines 200, 202, 204, respectively) return to approximate their initial, substantially stable values, indicative of their state change (e.g., re-emergence from introducer sheath 35). Only electrode 56 remains subject to an unreliable in-phase component (line 106) and a measurably changed quadrature component (line 206) because only electrode 56 remains within introducer sheath 35.

Figure 5:
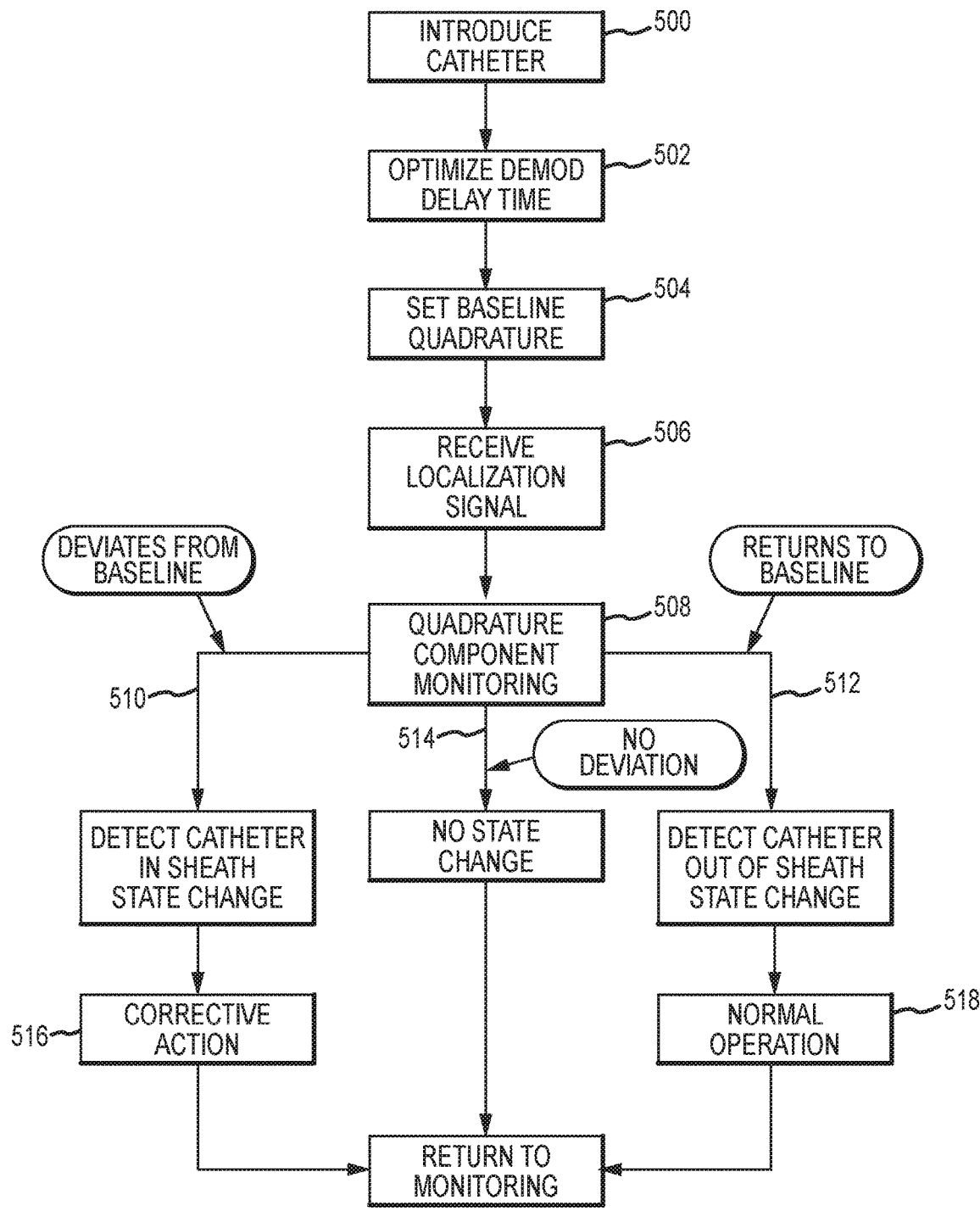
FIG. 5 is a flowchart depicting representative steps according to the teachings herein.

FIG. 5 is a flowchart of representative steps that can be performed in order to detect localization element/sheath state changes. In step 500, catheter 13 is introduced into the localization field generated by localization system 8 (e.g., introduced into the patient's heart). In optional step 502, the delay time of the demodulation signal is optimized. These steps are sufficiently well understood by those of ordinary skill in the art that they need not be further discussed herein.

In step 504, a baseline quadrature component is set, such that localization element/sheath state changes can be detected from the quadrature component of the localization signal for a catheter-borne localization element by comparisons between the real time quadrature component and the baseline quadrature component. The baseline is established with the localization element outside of the introducer sheath.

In one embodiment, the baseline quadrature component will follow from the optimization of the demodulation delay time in step 502. Typically, in a properly calibrated (that is, optimized) system, the quadrature component of the localization signal will remain substantially constant at a calibration value as the localization element moves. Localization element movement during calibration can be due to the patient's natural motion (e.g., the beating of the heart). Alternatively, it can be induced, such as by the practitioner making small movements of the catheter. The calibration value for the quadrature component is depicted, for example, in the lower window of FIG. 4 from time $t_0$ to time $t_2$.

As described above, optimization step 502 is optional. Thus, in certain embodiments, the demodulation delay is calculated using a calibration procedure ex vivo. One manner for sufficiently calibrating or "tuning" the localization system involves performing a standard calibration that approximates the delays experienced by the signals in the body, obtaining impedance measurements for both in-phase and out-of-phase with simulated patient impedances, until the out-of-phase signal shows minimal change with simulated location change. As described above, the "location change" can result from normal cardiac rhythm, manual movements of the catheter, and the like. Simulated location changes can be created by invoking small changes in the simulated patient impedance.

Once the baseline quadrature component (e.g., the calibration value) is established, localization element/sheath state changes can be detected from a received localization signal (step 506) by monitoring the quadrature component. (step 508) thereof.

For example, the withdrawal of a localization element into the introducer sheath can be detected when the quadrature component for the localization element deviates from the calibration value by more than a preset amount (path 510). This preset amount can be user-adjustable or user-selectable.

Conversely, when the quadrature component returns to within a preset amount of the calibration value (path 512), the re-emergence of the localization element from the introducer sheath can be detected.

Similarly, if no change in the quadrature component is detected (path 514), then no localization element/sheath state change is detected.

In response to detecting that a localization element/sheath state change, a number of steps (referred to generally as "corrective actions") can optionally be taken in step 516, either independently or in concert. For example, an alert (e.g., an audible, visual, and/or haptic signal) can be generated to call the practitioner's attention to the withdrawal of a localization element into, or emergence of a localization element from, the introducer sheath.

As another example, data collection can be gated to the in- or out-of-sheath state of a given localization element. That is, when the localization element is within the sheath, data collection therefrom can be suspended; when the localization element is outside of the sheath, data collection therefrom can proceed (step 518).

As still another example, data collected with the localization element within the sheath can simply be discarded.

Although several embodiments of this invention have been described above with a certain degree of particularity, those skilled in the art could make numerous alterations to the disclosed embodiments without departing from the spirit or scope of this invention.

For example, the invention has been described above with reference to the neck-leg axis. The use of the neck-leg axis is desirable because it helps ensure that the quadrature component will be non-zero, because there will be an offset between the location of catheter 13 (e.g., within the heart) and the coordinate reference point for the localization system (e.g., belly patch 21) that will be larger than on other axes. It should be understood, however, that the teachings herein could be applied to any or all measurement axes of localization system 8.

As another example, in another embodiment, the calibration process (502) does not change the demodulation delay time, but rather invokes a linear relationship between the in-phase and quadrature components of localization elements that are not in sheaths. When measuring complex impedance components, any calibration delay offset manifests as a quadrature component that is linearly dependent on the in-phase component. In addition, some constant current may be present in the instrumentation which is out of phase with the localization field generation, resulting in a position-independent quadrature measurement. The plurality of localization elements disposed within the localization field provides a plurality of co-located in-phase and quadrature measurements to which a linear model is fit, such as by using least-squares or another suitable model fitting technique. Alternately, a single localization element may be moved to a plurality of locations in order to acquire a number of co-located in-phase and quadrature measurements to determine the linear model parameters. Once the linear model parameters have been determined, a localization element can be identified as entering the sheath when its in-phase and quadrature measurements no longer fit the parameters, as evidenced by a residual between modeled and measured quadrature values rising above a critical threshold. An ordinarily skilled artisan would be able to extend the described technique to non-linear and multivariate models.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of detecting a localization element/sheath state change with a localization system, comprising:
    establishing a localization field using a plurality of localization field generators;
    obtaining at least one localization signal from at least one catheter-borne localization element positioned within the localization field via an introducer sheath, the at least one localization signal including an in-phase component and a quadrature component; and
    detecting a localization element/sheath state change for the at least one catheter-borne localization element based on the quadrature component of the at least one localization signal.

2. The method according to claim 1, wherein detecting a localization element/sheath state change comprises detecting the localization element/sheath state change for the at least one catheter-borne localization element based on a change in a value of the quadrature component of the at least one localization signal.

3. The method according to claim 2, wherein the change in the value of the quadrature component of the at least one localization signal is measured relative to a reference value of the quadrature component of the at least one localization signal.

4. The method according to claim 3, wherein the reference value comprises a baseline quadrature component established with the at least one localization element outside of the introducer sheath.

5. The method according to claim 3, wherein detecting the localization element/sheath state change for the at least one catheter-borne localization element based on the change in the value of the quadrature component of the at least one localization signal comprises detecting withdrawal of the at least one localization element into the introducer sheath when the change in the value of the quadrature component, measured relative to the reference value of the quadrature component of the at least one localization signal, begins to exceed a preset amount.

6. The method according to claim 3, wherein detecting the localization element/sheath state change for the at least one catheter-borne localization element based on the change in the value of the quadrature component of the at least one localization signal comprises detecting emergence of the at least one localization element from the introducer sheath when the change in the value of the quadrature component, measured relative to the reference value of the quadrature component of the at least one localization signal, ceases to exceed a preset amount.

7. A method of conducting a cardiac electrophysiology study, comprising:
    establishing an impedance-based localization field encompassing a patient's body;
    obtaining a localization signal from at least one localization element on at least one medical device positioned in the patient's body via an introducer sheath, the localization signal including an in-phase component reflecting a position of the at least one localization element within the localization filed and a quadrature component; and detecting whether the at least one localization element is within or outside of the introducer sheath based upon the quadrature component of the localization signal.

8. The method according to claim 7, further comprising generating an alert if the at least one localization element is detected within the introducer sheath.

9. The method according to claim 7, wherein detecting whether the at least one localization element is within or outside of the introducer sheath comprises analyzing a change in a value of the quadrature component of the localization signal.

10. The method according to claim 9, wherein the change in the value of the quadrature component of the localization signal is measured relative to a reference value of the quadrature component of the localization signal.

11. The method according to claim 10, wherein the reference value comprises a baseline quadrature component established with the at least one localization element outside of the introducer sheath.

12. The method according to claim 10, wherein the at least one localization element is detected as within the introducer sheath when the change in the value of the quadrature component of the localization signal measured relative to the reference value of the quadrature component of the localization signal exceeds a preset amount.

13. The method according to claim 10, wherein the at least one localization element is detected as outside of the introducer sheath when the change in the value of the quadrature component of the localization signal measured relative to the reference value of the quadrature component of the localization signal does not exceed a preset amount.

14. A localization system, comprising:
 a localization processor configured to receive as input a localization signal from at least one localization element and to resolve the localization signal into an in-phase component reflective of a position of the at least one localization element and a quadrature component; and
 a localization element/sheath state detection processor configured to receive as input the quadrature component and detect therefrom whether the at least one localization element is within an introducer sheath or outside of the introducer sheath.

15. The system according to claim 14, wherein the reference value comprises a baseline quadrature component established with the at least one localization element outside of the introducer sheath.

16. The system according to claim 15, wherein the baseline quadrature component is established by adjusting a demodulation delay for the localization signal until the quadrature component remains substantially constant at a calibration value as the at least one localization element moves.

17. The system according to claim 15, wherein the baseline quadrature component is established by making a plurality of complex impedance measurements and determining least squares parameters in a linear model.

* * * * *